United States Patent [19]

Ishikawa et al.

[11] 4,451,467
[45] May 29, 1984

[54] 4(3H)-QUINAZOLINONE DERIVATIVES, PROCESS FOR PRODUCTION THEREOF, AND PHARMACEUTICAL COMPOSITIONS COMPRISING SAID COMPOUNDS

[75] Inventors: Masayuki Ishikawa, 14-13, Akazutsumi 3-chome, Setagaya-ku, Tokyo, Japan; Yukuo Eguchi, Chiba, Japan; Soyao Moriguchi, Yokohama, Japan; Hisashi Ebisawa, Chofu, Japan

[73] Assignee: Masayuki Ishikawa, Tokyo, Japan

[21] Appl. No.: 337,454

[22] Filed: Jan. 6, 1982

[30] Foreign Application Priority Data

Jan. 16, 1981 [JP] Japan .................................. 56-3904
Aug. 4, 1981 [JP] Japan .................................. 56-121379
Sep. 18, 1981 [JP] Japan .................................. 56-146301

[51] Int. Cl.$^3$ .................. A61K 31/505; C07D 401/12; C07D 239/90
[52] U.S. Cl. ............................ 424/251; 544/284; 544/290
[58] Field of Search ................ 544/284, 290; 424/251

[56] References Cited

U.S. PATENT DOCUMENTS

4,183,931 1/1980 Wolfe et al. ................ 544/284
4,276,295 6/1981 Ishikawa et al. ............ 544/284

FOREIGN PATENT DOCUMENTS

42-12911 7/1967 Japan ........................... 544/290
7308045 12/1973 Netherlands ................. 544/290

OTHER PUBLICATIONS

Balasubramanian, "Indian J. Chem." vol. 12, No. 2, 1974, pp. 223–224.

Primary Examiner—Alton Q. Rollins
Assistant Examiner—James H. Turnipseed
Attorney, Agent, or Firm—Sherman & Shalloway

[57] ABSTRACT

The 4(3H)-quinazolinone compounds of the formula (I)

wherein
$R_1$ and $R_3$, independently from each other, represent a lower alkyl group;
$R_2$ represents a lower alkoxycarbonyl group;
Q represents a phenyl group or a substituted phenyl group substituted by at least one member selected from the group consisting of halogen atoms, lower alkyl groups, lower alkoxy groups, di(lower)alkylamino groups, a methylenedioxy group, a trifluoromethyl group, a hydroxyl group, and a nitro group;
$R_4$ represents a hydrogen atom or a lower alkyl group;
$R_5$ represents a member selected from the group consisting of a hydrogen atom, lower alkyl groups, lower halogenoalkyl groups, lower alkenyl groups, (lower)alkoxy(lower)alkyl groups, hydroxy(lower)alkyl groups, (lower)alkylthio(lower)alkyl groups, (lower)alkylsulfinyl(lower)alkyl groups, (lower)alkylsulfonyl(lower)alkyl groups, di(lower)alkylamino(lower)alkyl groups, a benzyl group, a phenethyl group, pyridyl(lower)alkyl groups, furfuryl groups, a phenyl group, and substituted phenyl groups substituted by a member selected from the group consisting of halogen atoms, lower alkyl groups, and lower alkoxy groups; and
$Z_1$ and $Z_2$, independently from each other, represent an oxygen or sulfur atom;
and an acid addition salt thereof; and a process for producing the same.

19 Claims, No Drawings

4(3H)-QUINAZOLINONE DERIVATIVES, PROCESS FOR PRODUCTION THEREOF, AND PHARMACEUTICAL COMPOSITIONS COMPRISING SAID COMPOUNDS

This invention relates to novel 4(3H)-quinazolinone derivatives which are useful as hypotensive agents for the treatment of hypertensive diseases.

More specifically, this invention relates to 4(3H)-quinazolinones of the formula

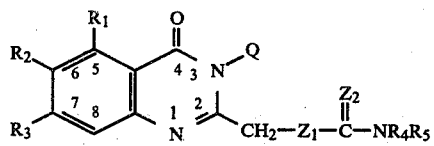

wherein
- $R_1$ and $R_3$, independently from each other, represent a lower alkyl group;
- $R_2$ represents a lower alkoxycarbonyl group;
- Q represents a phenyl group or a substituted phenyl group substituted by at least one member selected from the group consisting of halogen atoms, lower alkyl groups, lower alkoxy groups, di(lower)-alkylamino groups, a methylenedioxy group, a trifluoromethyl group, a hydroxyl group, and a nitro group;
- $R_4$ represents a hydrogen atom or a lower alkyl group;
- $R_5$ represents a member selected from the group consisting of a hydrogen atom, lower alkyl groups, lower halogenoalkyl groups, lower alkenyl groups, (lower)alkoxy(lower)alkyl groups, hydroxy(lower)alkyl groups, (lower)alkylthio(lower)alkyl groups, (lower)alkylsulfinyl(lower)alkyl groups, (lower)alkylsulfonyl(lower)alkyl groups, di(lower)alkylamino(lower)alkyl groups, a benzyl group, a phenethyl group, pyridyl(lower)alkyl groups, furfuryl groups, a phenyl group, and substituted phenyl groups substituted by a member selected from the group consisting of halogen atoms, lower alkyl groups, and lower alkoxy groups; and
- $Z_1$ and $Z_2$, independently from each other, represent an oxygen or sulfur atom;

and acid addition salts thereof.

This invention also relates to a process for producing the above novel compounds and their use as hypotensive agents.

U.S. Pat. No. 4,276,295 described 6-alkoxycarbonyl-5,7-dialkyl- or 7-alkoxycarbonyl-6,8-dialkyl-4(3H)-quinazolinone derivatives substituted with an aromatic moiety at the 3-position as vasodilators, hypotensive and anti-atherosclerotic agents. Subsequently, it was reported that 6-alkoxycarbonyl-5,7-dialkyl-2,4-(1H, 3H)-quinazolinedione derivatives bearing an aromatic moiety at the 3-position exhibit vasodilating, hypotensive, and antiatherosclerotic activities (U.S. patent application Ser. No. 263,898) filed May 15, 1981, now U.S. Pat. No. 4,405,623 issued Sept. 20, 1983.

The present inventors have now found that the 4(3H)-quinazolinone derivatives of formula (I) and the acid addition salts thereof which are not described in the literature can be easily synthesized, and have more potent hypotensive activity, better pharmacological profiles and lower toxicity as hypotensive agents, than the prior art compounds described above. It has also been found that the compounds of the present invention have a high degree of hypotensive activity both in anesthetized rabbits by intravenous administration and in conscious spontaneously hypertensive rats in oral administration. The hypotensive activity of the compounds of the present invention is approximately at least ten to hundred times as potent as that of the 4(3H)-quinazolinone and 2,4(1H, 3H)-quinazolinedione derivatives cited above. Furthermore, the hypotensive effect of the compounds of the present invention is longer lasting than that of the compounds of the prior art described above. The compounds of the invention are thus highly desirable as pharmaceutical agents for use in the treatment of hypertensive diseases.

It is an object of this invention therefore to provide the novel 4(3H)-quinazolinone derivatives of formula (I) and the acid addition salts thereof.

Another object of this invention is to provide a hypotensive agent comprising the compound of formula (I) as an active ingredient, which is useful for the treatment of hypertension and the like.

Still another object of this invention is to provide a process for producing the compounds of formula (I).

The above and other objects and advantages of this invention will become more apparent from the following description.

The compounds of this invention are expressed by the following formula

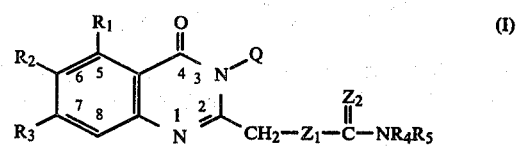

In formula (I), $R_1$ and $R_3$ represent a lower alkyl group, preferably a $C_1$-$C_3$ alkyl group such as a methyl, ethyl and propyl group, and $R_2$ represents a lower alkoxycarbonyl group, preferably an alkoxycarbonyl group having a $C_1$-$C_4$ alkoxy group which may be linear or branched, such as a methoxy, ethoxy, propoxy, isopropoxy, n-butoxy or isobutoxy group.

In formula (I), Q represents a phenyl group or a substituted phenyl group substituted by at least one member selected from the group consisting of halogen atoms such as chlorine, bromine and fluorine atom, lower alkyl groups, preferably $C_1$-$C_3$ alkyl groups, as exemplified in $R_1$ and $R_3$, lower alkoxy groups, preferably $C_1$-$C_4$ alkoxy groups, as exemplified in $R_2$, di-lower-alkylamino groups, preferably having $C_1$-$C_3$ alkyl grcups, as exemplified in $R_1$ and $R_3$, a methylenedioxy group, a trifluoromethyl group, a hydroxyl group and a nitro group.

In formula (I), $R_4$ represents a hydrogen atom or a lower alkyl group, preferably a $C_1$-$C_3$ alkyl group as exemplified in $R_1$ and $R_3$, $R_5$ represents a member selected from the group consisting of a hydrogen atom, lower alkyl groups, preferably $C_1$-$C_7$ alkyl groups such as a methyl, ethyl, propyl, isopropyl, butyl, isobutyl, bert-butyl, amyl, isoamyl, hexyl, cyclohexyl or cyclohexylmethyl group, lower halogenoalkyl groups, preferably halogeno($C_1$-$C_4$)-alkyl groups such as a fluoromethyl, 2-fluoroethyl, 3-fluoropropyl, 2-chloroethyl, 3-chloropropyl or 3-bromoethyl group, lower alkenyl groups, preferably $C_3$-$C_6$ alkenyl groups such as an allyl, 2-butenyl, 3-hexenyl or cyclohexenyl group, lower alkoxy-lower alkyl groups, preferably ($C_1$–$C_3$)alkoxy($C_1$–$C_4$)alkyl groups, lower hydroxyalkyl groups, preferably hydroxy($C_1$–$C_4$)alkyl groups, lower alkylthio-lower alkyl groups, preferably ($C_1$–$C_3$)alkylthio($C_1$–$C_4$)alkyl groups, lower alkylsulfinyl-lower alkyl groups, preferably ($C_1$–$C_3$)alkylsulfinyl($C_1$–$C_4$)alkyl groups, lower alkylsulfonyl-lower alkyl groups, preferably ($C_1$–$C_3$)alkylsulfonyl($C_1$–$C_4$)alkyl groups, di-lower-alkylamino-loweralkyl groups, preferably di-($C_1$–$C_3$)alkylamino($C_1$–$C_4$)alkyl groups, a benzyl group, a phenethyl group, pyridyl-lower alkyl groups, preferably 2-, 3- or 4-pyridylmethyl groups, furfuryl groups such as 2-, 3- or 4-furfuryl group, a phenyl group and substituted phenyl groups substituted by a member selected from the group consisting of halogen atoms such as chlorine, bromine and fluorine atom, lower alkyl groups, preferably $C_1$–$C_2$ alkyl groups and lower alkoxy groups, preferably ($C_1$–$C_3$)alkoxy groups.

In formula (I), $Z_1$ and $Z_2$, independently from each other, represent an oxygen atom or a sulfur atom.

The above compounds of formula (I) and their acid addition salts can be prepared by any of the following processes:

(a) A compound of the general formula

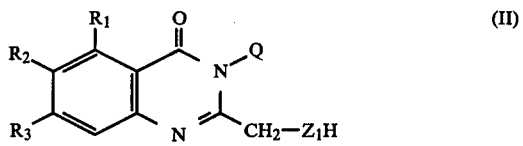

(II)

wherein $R_1$, $R_2$, $R_3$, Q, and $Z_1$ are the same as defined above, is reacted with a compound of the formula:

$$R_5NC=Z_2 \quad (III)$$

wherein $R_5$ is as defined above excepting hydrogen and $Z_2$ is the same as defined above to give a compound of general formula (I) wherein $R_4$ is a hydrogen atom; or (b) a compound of formula (II) is reacted with a compound of the formula:

(IV)

wherein $R_4$, $R_5$, and $Z_2$ are as defined above, and Y is a halogen atom or an alkoxy, aryloxy, alkylthio or arylthio group; or (c) a compound of formula (II) is reacted in the presence of a dehydrochlorinating agent with a compound of the general formula:

(V)

wherein $Z_2$ and Y are as defined above, and then the resulting product is reacted with ammonia or an amine of the general formula:

$$NHR_4R_5 \quad (VI)$$

wherein $R_4$ and $R_5$ are as defined above.

The compounds of the present invention can be prepared by any of the processes described above. The compounds prepared by the above processes are new, and in experiments using rats, rabbits, and dogs, they showed profound hypotensive activity both in vitro and in vivo. Therefore, the compounds of this invention are useful for the treatment of hypertensive diseases.

The starting material of formula (II) can be manufactured by the methods described in the specification of U.S. Pat. No. 4,276,295. The compound of formula (II) wherein $Z_1$ is a sulfur atom can be preferably manufactured by treating a 2-bromomethyl compound with sodium thioacetate in dimethylformamide and then reacting the resulting product with ammonia. In most cases the 2-mercaptomethyl compound is sensitive to oxidation, and therefore it is preferred to proceed to the next step without isolation and purification of the mercaptomethyl compound. The processes for the manufacture of the compound of (II) can be summarized by the following reaction scheme wherein $R_1$, $R_2$, $R_3$, and Q are as defined above.

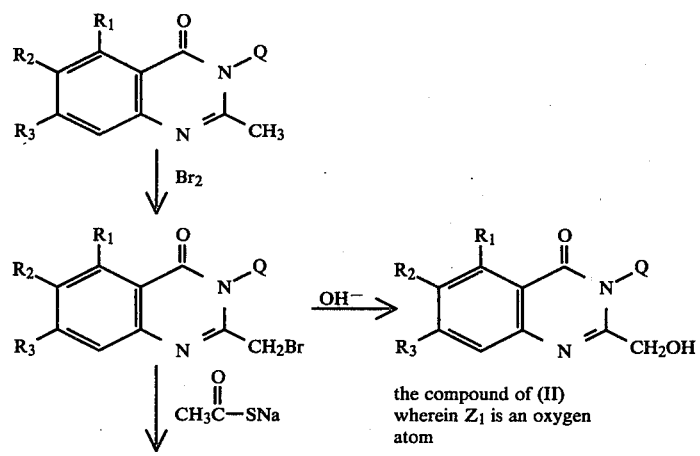

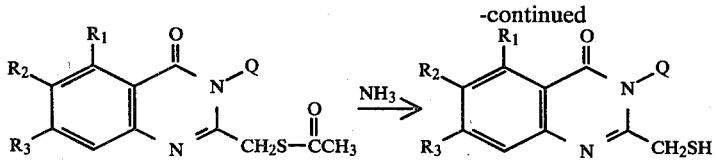

the compound of (II) wherein $Z_1$ is a sulfur atom

Examples of the compounds represented by formula (II) include 3-(2-chlorophenyl)-6-ethoxycarbonyl-2-hydroxymethyl-5,7-dimethyl-4(3H)-quinazolinone, 6-ethoxycarbonyl-3-(2-fluorophenyl)-2-hydroxymethyl-5,7-dimethyl-4(3H)-quinazolinone, 3-(2-bromophenyl)-6-ethoxy-carbonyl-2-hydroxymethyl-5,7-dimethyl-4(3H)-quinazolinone, 6-ethoxycarbonyl-2-hydroxymethyl-5,7-dimethyl-3-(2-methylphenyl)-4(3H)-quinazolinone, 6-ethoxycarbonyl-3-[2-(trifluoromethyl)phenyl]-2-hydroxymethyl-5,7-dimethyl-4(3H)-quinazolinone, 6-ethoxycarbonyl-2-hydroxymethyl-5,7-dimethyl-3-(2-nitrophenyl)-4(3H)-quinazolinone, 6-ethoxycarbonyl-2-hydroxymethyl-3-(2-methoxyphenyl)-5,7-dimethyl-4(3H)-quinazolinone, 3-(2-ethoxyphenyl)-6-ethoxycarbonyl-2-hydroxymethyl-5,7-dimethyl-4(3H)-quinazolinone, 6-ethoxycarbonyl-2-hydroxymethyl-5,7-dimethyl-3-(2,3-, 2,4-, 2,5-, or 2,6-dimethylphenyl)-4(3H)-quinazolinone, 3-(2,4-, 2,5-, or 2,6-dichlorophenyl)-6-ethoxycarbonyl-2-hydroxymethyl-5,7-dimethyl-4(3H)-quinazolinone, 6-ethoxycarbonyl-2-hydroxymethyl-3-(3,4-dimethoxyphenyl)-5,7-dimethyl-4(3H)-quinazolinone, 6-ethoxycarbonyl-2-hydroxymethyl-5,7-dimethyl-3-(3,4-methylenedioxyphenyl)-4(3H)-quinazolinone, 6-ethoxycarbonyl-2-hydroxymethyl-5,7-dimethyl-3-(3,4,5-trimethoxyphenyl)-4(3H)-quinazolinone, 3-(2-chloro-5-methoxyphenyl)-6-ethoxycarbonyl-2-hydroxymethyl-5,7-dimethyl-4(3H)-quinazolinone, 6-ethoxycarbonyl-2-hydroxymethyl-3-(4-methoxy-2-methylphenyl)-5,7-dimethyl-4(3H)-quinazolinone, 6-ethoxycarbonyl-3-(4-hydroxy-2-methylphenyl)-2-hydroxymethyl-5,7-dimethyl-4(3H)-quinazolinone, 3-(3-chloro-2-methyl- or 4-chloro-2-methylphenyl)-6-ethoxycarbonyl-2-hydroxymethyl-5,7-dimethyl-4(3H)-quinazolinone, 3-(5-chloro-2-methoxyphenyl)-6-ethoxycarbonyl-2-hydroxymethyl-5,7-dimethyl-4(3H)-quinazolinone, 6-ethoxycarbonyl-2-hydroxymethyl-5,7-dimethyl-3-[2-, 3-, or 4-(dimethylamino)phenyl]-4(3H)-quinazolinone, 3-(2-chlorophenyl)-2-hydroxymethyl-5,7-dimethyl-6-propoxycarbonyl-4(3H)-quinazolinone, 3-(2-chlorophenyl)-2-hydroxymethyl-6-isopropoxycarbonyl-5,7-dimethyl-4(3H)-quinazolinone, 6-butoxycarbonyl-3-(2-chlorophenyl)-5,7-dimethyl-2-hydroxymethyl-4(3H)-quinazolinone, 3-(2-chlorophenyl)-2-hydroxymethyl-6-isobutoxycarbonyl-5,7-dimethyl-4(3H)-quinazolinone, 3-(2-chlorophenyl)-6-ethoxycarbonyl-2-mercaptomethyl-5,7-dimethyl-4(3H)-quinazolinone, 3-(2-bromophenyl)-6-ethoxycarbonyl-2-mercaptomethyl-5,7-dimethyl-4(3H)-quinazolinone, 6-ethoxycarbonyl-2-mercaptomethyl-5,7-dimethyl-3-(2-methylphenyl)-4(3H)-quinazolinone, and 6-ethoxycarbonyl-2-mercaptomethyl-5,7-dimethyl-3-(2-, 3-, and 4-nitrophenyl)-4(3H)-quinazolinone.

In process (a), the compound of (II) may be reacted with the compound of (III) in an inert solvent or diluent, such as benzene, toluene, chlorobenzene, chloroform, dioxane, tetrahydrofuran, ether, ethyl acetate, acetonitrile or pyridine. The compound (III) may be used in an amount of, say, 1 to 5 moles, preferably 1.2 to 2 moles per mole of the compound (II). Preferably, the compound of formula (III) is used in a molar excess. The reaction is preferably carried out at room temperature to about 150° C., especially about 50°–about 100° C., and the reaction is usually completed in about 1 to about 5 hours at around 80° C. At room temperature a longer reaction time, for example about 5 to about 24 hours, is preferred. A catalyst such as a tertiary amine (e.g. trimethylamine, triethylamine, N-methylpiperidine, N-ethylpiperidine, dimethylaniline, pyridine or 4-dimethylaminopyridine) is preferably used.

Examples of the compound (III) include isocyanates such as methyl-, ethyl-, n-propyl-, isopropyl-, n-butyl-, isobutyl-, tertbutyl-, n-amyl-, isoamyl-, n-hexyl-, cyclohexyl-, cyclohexylmethyl-, 2-(methoxy)ethyl-, 2-(ethoxy)ethyl-, 3-(methoxy)propyl-, 3-(ethoxy)propyl-, 4-(methoxy)butyl-, 4-(ethoxy)butyl-, methylthiomethyl-, 2-(methylthio)ethyl-, 3-(methylthio)propyl-, ethylthiomethyl-, 2-(ethylthio)ethyl-, 3-(ethylthio)propyl-, methylsulfinylmethyl-, 2-(methylsulfinyl)ethyl-, 3-(methylsulfinyl)propyl-, ethylsulfinylmethyl-, 2-(ethylsulfinyl)ethyl-, methylsulfonylmethyl-, 2-(methylsulfonyl)ethyl-, 3-(methylsulfonyl)propyl-, ethylsulfonylmethyl-, 2-(ethylsulfonyl)ethyl-, 2-(dimethylamino)ethyl-, 2-(diethylamino)ethyl-, 3-(dimethylamino)propyl-, 3-(diethylamino)propyl-, 4-(dimethylamino)butyl-, 4-(diethylamino)butyl-, phenyl-, o-, m- and p-tolyl-, o-, m- and p-chlorophenyl-, o-, m- and p-methoxyphenyl-, benzyl-, phenethyl-, 2-, 3- and 4-pyridyl-, 2-, 3- and 4-pyridylmethyl-isocyanates. Isothiocyanates such as methyl-, ethyl-, n-propyl- and isopropyl-isothiocyanates can also be included in the examples of the compound of (III).

In place of the isocyanate (III), a compound which can be converted to the isocyanate of formula (III) under the reaction conditions can also be used, and if necessary a catalyst to generate the isocyanate in situ may be used. For example, an acyl azide of the formula

wherein $R_5$ is as defined above excepting a hydrogen atom, or an S-alkyl thiocarbamate of the formula:

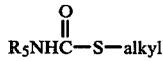

wherein $R_5$ is as defined above excepting a hydrogen atom, and the term "alkyl" means a lower alkyl group such as a methyl or ethyl group, may be heated to give the corresponding isocyanate. S-alkyl thiocarbamates may also be used in the presence of a trialkylamine and a heavy metal salt such as silver nitrate.

Accordingly, in the invention, the reaction of the compound of formula (II) with the compound of formula (III) also includes the reaction of the compound (II) with a compound capable of being converted to the compound of formula (III) under the reaction conditions. Process (a) can only be used to make compounds of formula (I) in which $R_4$ is a hydrogen atom, and $R_5$ is not a hydrogen atom.

In process (b), the compound of (II) may be reacted with the compound of (IV) in an inert solvent or diluent, such as benzene, toluene, chlorobenzene, chloroform, dioxane, tetrahydrofuran, acetonitrile, dimethylformamide or pyridine. The compound (IV) may be used in an amount of, for example, 1 to 5 moles, preferably 1.2 to 2 moles per mole of the compound (II). Preferably, the compound (IV) is used in a molar excess. The reaction is preferably carried out at about 50° to about 150° C., especially about 50°–about 100° C., the reaction is usually completed in about 1 to about 5 hours. A catalyst such as N-methylpiperidine, N-ethylpiperidine, dimethylaniline, pyridine or 4-dimethylaminopyridine is preferably used.

Examples of the compound of (IV) include N,N-dimethylcarbamoyl chloride, N,N-diethylcarbamoyl chloride, N,N-dipropylcarbamoyl chloride, N,N-diisopropylcarbamoyl chloride, N-butyl-N-methylcarbamoyl chloride, N-butyl-N-ethylcarbamoyl chloride, N-methyl-N-propylcarbamoyl chloride, N-ethyl-N-methylcarbamoyl chloride, N-methyl-N-[2-(methoxy)ethyl]-carbamoyl chloride, N-methyl-N-[2-(ethoxy)ethyl]carbamoyl chloride, N-methyl-N-(methylthiomethyl)carbamoyl chloride, N-methyl-N-(ethylthioethyl)-carbamoyl chloride, N-methyl-N-[2-(dimethylamino)ethyl]carbamoyl chloride, N-methyl-N-phenylcarbamoyl chloride, N-(o-, m- and p-chlorophenyl)-N-methylcarbamoyl chloride, N-(o-, m- and p-methoxyphenyl)-N-methylcarbamoyl chloride, N-benzyl-N-methylcarbamoyl chloride, N-methyl-N-(2-, 3- and 4-pyridyl)carbamoyl chloride, N-methyl-N-(2-, 3- and 4-pyridylmethyl)carbamoyl chloride, N,N-dimethylthiocarbamoyl chloride and N,N-diethylthiocarbamoyl chloride, and the bromides corresponding to the chlorides described above. Phenyl N-substituted carbamate such as phenyl N-methylcarbamate, phenyl N-ethylcarbamate, phenyl N-isopropylcarbamate and phenyl N,N-dimethylcarbamate, and alkyl N-substituted thiolcarbamate such as ethyl N-methylthiolcarbamate, ethyl N-ethylthiolcarbamate and ethyl N-propylthiolcarbamate, can also be used as the compound of (IV). In this case, the reaction can be carried out without solvent, simply by heating an equimolar mixture of the compound (II) and (IV) at about 100° to about 150° C.

In process (c), the compound of (II) may be reacted with the compound of (V) in an inert solvent, such as benzene, toluene, chloroform, dichloroethane, dioxane, tetrahydrofuran, ether, ethyl acetate, dimethylformamide, acetonitrile or pyridine, or mixtures thereof. The compound (V) may be used in an amount of, for example, 1.1 to 2 moles per mole of the compound (II). Preferably, it is used in a molar excess. To the reaction mixture, a dehydrochlorinating agent such as a tertiary amine, e.g. diethylamine, N-methylpiperidine, dimethylaniline or pyridine, is preferably added. Examples of the compound of (V) include phosgene, thiophosgene, phenyl chloroformate, p-chlorophenyl chloroformate, ethyl chloroformate, ethyl chlorothioformate and phenyl chlorothioformate. The reaction is preferably carried out at about −20° to about 100° C., especially about −10° to about 50° C. The reaction time is, for example, about 1 to 30 hours. At around 0° C., about 5 to about 24 hours is preferred. The resulting product of the above reaction [the compound of formula (VII) depicted in the reaction scheme given hereinbelow] is then reacted with ammonia or an amine of formula (VI).

When the compound of (V) is phosgene or thiophosgene, the intermediate compound of (VII) is preferably reacted with ammonia or an amine of (VI) in one-pot reaction without isolating the compound of (VII). In this case, as shown in the reaction scheme below, 2 moles of hydrochloric acid per mole of the compound of (II) is generated. Hence, it is preferably to use at least 2 moles of the dehydrochlorinating agent in the overall process.

When the compound of (V) is other than phosgene or thiophosgene, it is preferred to carry out the process through two independent steps, namely the reaction of the compound (II) with the compound (V) and the reaction of the intermediate compound (VII) with the amine of (VI). The intermediate compound (VII) is isolated and purified, if necessary, and then reacted with an excess, for example, 1.5–5 moles per mole of the compound of (VII) of ammonia or an amine of (VI) in a solvent or diluent, such as methanol, ethanol or propanol. The reaction can be carried out at room temperature to about 100° C., and ends in about 1 to about 24 hours, for example, depending on the reaction temperature.

Examples of the amine of (VI) include ammonia, methyl-, ethyl-, n-propyl-, isopropyl-, n-butyl-, isobutyl-, tert-butyl-, n-amyl-, isoamyl-, n-hexyl-, dimethyl-, diethyl- and dipropyl-amine; and 1-amino-2-hydroxyethane, 1-amino-3-hydroxypropane, 1-amino-4-hydroxybutane, 1-amino-2-methoxyethane, 1-amino-2-ethoxyethane, 1-amino-3-methoxypropane, 1-amino-3-ethoxypropane, 1-amino-4-methaoxybutane, 1-amino-4-ethoxybutane, methylthiomethylamine, 1-amino-2-methylthio)ethane, 1-amino-3-(methylthio)propane, ethylthiomethylamine, 1-amino-2-(ethylthio)ethane, 1-amino-3-(ethylthio)propane, methylfulfinylmethylamine, 1-amino-2-(methylfulfinyl)ethane, 1-amino-2-(ethylsulfonyl)ethane, 1-amino-2-(dimethylamino)ethane, 1-amino-2-(diethylamino)ethane, 1-amino-3-(dimethylamino)propane, 1-amino-3-(diethylamino)propane, 1-amino-4-(dimethylamino)butane, 1-amino-4-(diethylamino)butane, benzylamine, phenethylamine, 2-, 3- and 4-pyridylmethylamine.

The above processes (a)–(c) can be represented by the following reaction scheme wherein $R_1$, $R_2$, $R_3$, $R_4$, $R_5$, Q, $Z_1$, $Z_2$ and Y are as defined hereinbefore.

Process (a)

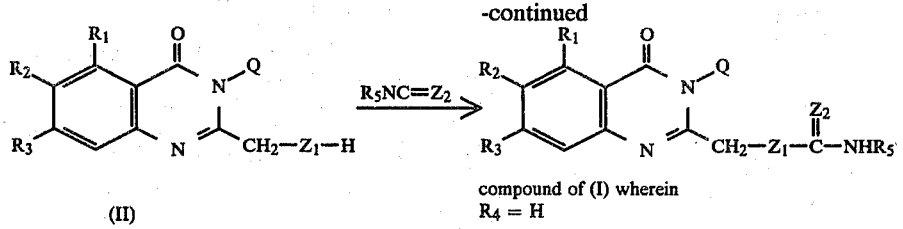

compound of (I) wherein $R_4 = H$

Process (b)

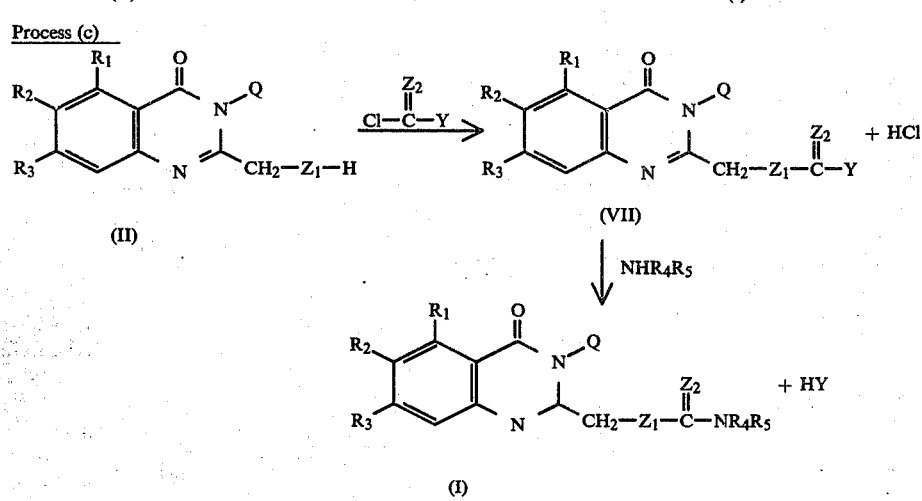

The product can be separated and purified by conventional methods as described hereinafter. If desired, the compound of formula (I) can be converted to its acid addition salt, preferably its pharmaceutically acceptable acid addition salt by conventional procedures. Examples of acids that can be used to form such a salt include inorganic acids such as hydrochloric acid, sulfuric acid and hydrobromic acid, and organic acids such as oxalic acid, maleic acid, malic acid and tartaric acid.

According to this invention, there is provided a hypotensive agent useful for the treatment of diseases caused by hypertension and the like, which comprises an effective amount of the 4(3H)-quinazolinone of formula (I) or its pharmaceutically acceptable acid addition salt, and a pharmaceutically acceptable liquid or solid diluent or carrier.

Examples of such pharmaceutically acceptable liquid or solid diluents or carriers include solid carriers such as sodium chloride, glucose, lactose, starch, sucrose, magnesium stearate, cetyl alcohol, cacao butter and spermaceti; and liquid carriers such as distilled water, isotonic sodium chloride solution, Ringer's solution, Locke's solution, polyethylene glycol, propylene glycol, ethyl alcohol, glycerol and vegetable oils.

The hypotensive agents of this invention may be in various formulations such as powders, granules, particles, tablets, capsules, troches, suspensions and solutions.

The dosage of the hypotensive agent of this invention is about 0.05 to about 10 mg/kg/day although it can be properly changed depending upon the type and extent of the patient's condition, the method of administration, etc.

The amount of the compound of formula (I) or its pharmaceutically acceptable acid addition salt to be included in the hypotensive agent of this invention can be properly changed according to the formulation of the hypotensive agent, the method of administration, etc. For example, it is about 1 to about 80% by weight based on the weight of the hypotensive agent.

Tests for pharmacological effects and for acute toxicity of several examples of the compounds of this invention are shown below under the headline "Test for biological effect" and "Test for acute toxicity".

The following Examples illustrate the production of the compounds of this invention.

EXAMPLE 1

Methyl isocyanate (40 mg) was added to a solution of 232 mg of 3-(2-chlorophenyl)-6-ethoxycarbonyl-2-hydroxymethyl-5,7-dimethyl-4(3H)-quinazolinone in 10 ml of ethyl acetate. After addition of a few drops of triethylamine, the reaction mixture was stirred at room temperature overnight. The solvent was then evaporated off and the residue was recrystallized from ethanol-n-hexane to give 160 mg (yield, 60.2%) of 3-(2-chlorophenyl)-6-ethoxycarbonyl-5,7-dimethyl-2-(N-methylcarbamoyloxymethyl)-4(3H)-quinazolinone melting at 183°–184° C. MS m/e, 443 (M+), 396 351.

NMR (ppm, in CDCl₃); 1.40 (3H, t), 2.42 (3H, s), 2.69 (3H, s), 2.71 (3H, d), 4.43 (2H, q), 4.70 (3H, d), 7.35–7.75 (5H, m).

EXAMPLE 2

Isopropyl isocyanate (52 mg) was added to a solution of 230 mg of 3-(2-chlorophenyl)-6-ethoxycarbonyl-2-hydroxymethyl-5,7-dimethyl-4(3H)-quinazolinone in 10 ml of pyridine. The reaction mixture was stirred at 70° C. for 3 hours and then concentrated under reduced pressure. The residue was recrystallized from diethyl ether-cyclohexane to give 152 mg (yield, 55.8%) of 3-(2-chlorophenyl)-6-ethoxycarbonyl-5,7-dimethyl-2-(N-isopropylcarbamoyloxymethyl)-4(3H)-quinazolinone melting at 134.5°–135.5° C.

EXAMPLE 3

N,N-Dimethylcarbamoyl chloride (200 mg) was added to a solution of 150 mg of 3-(2-chlorophenyl)-6-ethoxycarbonyl-2-hydroxymethyl-5,7-dimethyl-4(3H)-quinazolinone in 50 ml of pyridine. The reaction mixture was stirred at 80° C. for 3 hours, and the solvent was then distilled off under reduced pressure. The residue was extracted with diethyl ether, and the ether extract was washed successively with 1% aqueous hydrochloric acid and water, and dried over anhydrous sodium sulfate. The ether was evaporated off, and the residue was taken up with ethanyl containing 5% hydrochloric acid and concentrated to dryness. The residue was recrystallized from ethanol-n-hexane to give 77 mg (yield, 43.0%) of 3-(2-chlorophenyl)-2-(N,N-dimethylcarbamoyloxymethyl)-6-ethoxy-carbonyl-5,7-dimethyl-4(3H)-quinazolinone hydrochloride melting at 113°–115° (decomp.). MS m/e, 457 (M+), 422, 412, 385. NMR (ppm, in CDCl₃), 1.40 (3H, t), 2.42 (3H, s), 2.77 (3H, s), 2.92 (6H, s), 4.43 (2H, q), 4.72 (2H, s), 7.25–7.55 (5H, m).

EXAMPLE 4

Phenyl chloroformate (470 mg) was added to a solution of 420 mg of 6-ethoxycarbonyl-2-hydroxymethyl-5,7-dimethyl-3-[2-(trifluoromethyl)phenyl]-4(3H)-quinazolinone in 5 ml of pyridine. The reaction mixture was stirred at 80° C. for 3 hours, and the solvent was then evaporated off in vacuo. The residue was taken up with ethyl acetate, and the solution was washed successively with 1N aqueous hydrochloric acid and water, and dried over anhydrous sodium sulfate. The ethyl acetate was evaporated off to give 400 mg of crude 6-ethoxycarbonyl-5,7-dimethyl-2-(phenoxycarbonyloxymethyl)-3-[2-(trifluoromethyl)phenyl]-4(3H)-quinazolinone.

The product (400 mg) described above was dissolved in 20 ml of ethanol. To this solution, 5 ml of conc. aqueous ammonia was added, and the reaction mixture was stirred at 50° C. for 5 hours and concentrated. The concentrate was diluted with water and extracted with ethyl acetate. The ethyl acetate extract was dried over anhydrous sodium sulfate and concentrated. The residue was recrystallized from ethanol-n-hexane to give 175 mg (yield, 37.8%) of 2-carbamoyloxymethyl-6-ethoxycarbonyl-5,7-dimethyl-3-[2-(trifluoromethyl)phenyl]-4(3H)-quinazolinone melting at 158°–159° C.

EXAMPLE 5

A portion (360 mg) of 3-(2-chlorophenyl)-6-ethoxycarbonyl-5,7-dimethyl-2-(phenoxycarbonyloxymethyl)-4(3H)-quinazolinone prepared in a similar manner to Example 4 was dissolved in 10 ml of ethanol. To this solution, 1 g of N,N-dimethylethylenediamine was added. The reaction mixture was heated at 80° C. for 6 hours and then concentrated under reduced pressure. The residue was taken up with ether, and the ether extract was washed successively with 10% aqueous hydrochloric acid and water, dried over anhydrous sodium sulfate and concentrated. The resulting residue was chromatographed on silica gel with 5% ethanol in chloroform as an eluent to give an oily product. The oil was dissolved in ether, and to this solution 50 mg of oxalic acid was added. The resulting precipitate was filtered off and recrystallized from ethanol-ether to give 130 mg (yield, 31%) of 6-ethoxycarbonyl-5,7-dimethyl-3-(2-chlorophenyl)-2-[2-(N,N-dimethylamino)ethylcarbamoyloxymethyl]-6-ethoxycarbonyl-5,7-dimethyl-4(3H)-quinazolinone monooxalate melting at 158°–159° C.

EXAMPLE 6

A mixture consisting of 200 mg of 3-(2,6-dichlorophenyl)-6-ethoxycarbonyl-2-hydroxymethyl-5,7-dimethyl-4(3H)-quinazolinone, 100 mg of isopropyl isocyanate, and 3 ml of pyridine was heated at 70° C. for 3 hours. After evaporating off the pyridine at reduced pressure, the residue was taken up with ethyl acetate. The ethyl acetate solution was then washed with water, dried over anhydrous sodium sulfate and concentrated. The residue was dissolved in 5 ml of ethanol containing 10% hydrochloric acid, and the solvent was evaporated off. The residue was recrystallized from ethanol-ether to give 3-(2,6-dichlorophenyl)-6-ethoxycarbonyl-2-(N-isopropylcarbamoyloxymethyl)-5,7-dimethyl-4(3H)-quinazolinone monohydrochloride melting at 136–138 (decomp.). The yield was 140 mg (54%). MS m/e, 505 (M+), 462, 460, 420, 385. NMR (ppm, in CDCl₃), 1.14 (6H, d), 1.40 (3H, t), 2.43 (3H, s), 2.78 (3H, s), 3.70 (1H, m), 4.44 (2H, q), 4.71 (2H, s), 7.35–7.55 (4H, m).

EXAMPLE 7

A mixture consisting of 193 mg of 3-(2-chlorophenyl)-6-ethoxycarbonyl-5,7-dimethyl-2-hydroxymethyl-4(3H)-quinazolinone, 0.3 ml of methyl isothiocyanate, 10 mg of 4-dimethylaminopyridine, and 10 ml of anhydrous pyridine was heated under reflux for 20 hours. After cooling, the solvent was evaporated off in vacuo. The residue was taken up with chloroform, and the chloroform extract was washed successively with 10% aqueous hydrochloric acid, saturated aqueous sodium hydrogencarbonate, and water. After drying over anhydrous sodium sulfate, the solvent was evaporated off. The residue was chromatographed on silica gel using benzene-chloroform mixture (v/v, 6:4) as an eluent to give 90 mg (yield, 39.1%) of 3-(2-chlorophenyl)-6-ethoxycarbonyl-5,7-dimethyl-2-(N-methylthiocarbamoyloxymethyl)-4(3H)-quinazolinone melting at 164°–165° C. (recrystallized from methanol-n-hexane).

EXAMPLE 8

In a similar manner to Example 7, 3-(2-chlorophenyl)-6-ethoxycarbonyl-5,7-dimethyl-2-hydroxymethyl-4(3H)-quinazolinone was reacted with ethyl isothiocyanate, and the reaction mixture was similarly worked up. The crude product was chromatographed on silica gel and the residue obtained from the eluate was treated with ethanol containing hydrochloric acid and recrystallized from ethanol-ether to give 3-(2- chlorophenyl)-6-ethoxycarbonyl-2-(N-ethylthiocarbamoyloxymethyl)-5,7-dimethyl-4(3H)-quinazolinone hydrochloride melting at 156°–159° C. (decomp.).

EXAMPLES 9–45

In a similar manner to Example 1–7, the following compounds of formula (Ia) wherein R is a substituent or substituents on the 3-phenyl group were obtained in a yield of 40–80% as shown in Table I.

TABLE I

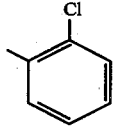

(Ia)

| | Compound of formula (Ia) | | | | Recryst. |
|---|---|---|---|---|---|
| No. | R | $R_4$ | $R_5$ | Melting point (°C.) | Solvent |
| 9 | 2-Cl | H | $C_2H_5$ | 108–110: hydrochloride: 168–172 (decomp.) | ethanol/hexane (ethanol/ether) |
| 10 | " | " | n-$C_3H_7$ | hydrochloride: 144–146 (decomp.) | ethanol/ether |
| 11 | " | " | $CH_2CH=CH_2$ | hydrochloride: 139–141 (decomp.) | " |
| 12 | " | " | n-$C_4H_9$ | hydrochloride: 126–129 (decomp.) | " |
| 13 | " | " | i-$C_4H_9$ | hydrochloride: 157–159 (decomp.) | " |
| 14 | " | " | t-$C_4H_9$ | hydrochloride: 157–159 (decomp.) | " |
| 15 | " | " | n-$C_5H_{11}$ | hydrochloride: 115–118 (decomp.) | " |
| 16 | " | " | i-$C_5H_{11}$ | hydrochloride: 120–122 (decomp.) | " |
| 17 | H | " | $CH_3$ | hydrochloride: 168–172 (decomp.) | " |
| 18 | 2-F | " | i-$C_3H_7$ | hydrochloride: 145–147 | " |
| 19 | 2-Br | " | " | 146.5–147.5 | ether |
| 20 | 2-$CH_3O$ | " | " | 169–170.5 | ethanol/ether |
| 21 | 3-$CH_3O$ | " | $CH_3$ | hydrochloride: 132–134 (decomp.) | " |
| 22 | 4-$CH_3O$ | " | $CH_3$ | hydrochloride: 136–138 (decomp.) | " |
| 23 | 2-$CH_3$ | " | i-$C_3H_7$ | hydrochloride: 146–148 (decomp.) | " |
| 24 | 2-$C_2H_5$ | " | " | hydrochloride: 118–122 (decomp.) | ethanol |
| 25 | 2,6-$(CH_3)_2$ | " | i-$C_3H_7$ | 140–141 | " |
| 26 | 2-$CH_3$, 4-$(2H_5)_2N$ | " | " | dihydrochloride: 144–147 (decomp.) | ethanol/ether |
| 27 | 2-$CF_3$ | " | " | 99–100 | ethanol/n-hexane |
| 28 | 2-$NO_2$ | " | $C_2H_5$ | 108 | ethanol/n-hexane |
| 29 | 3,4-$(CH_3O)_2$ | " | $CH_3$ | 127–128 | ethanol/n-hexane |
| 30 | 3,4-methylenedioxy | " | " | 226–227 | ethanol |
| 31 | 2-Cl | " | $CH_2CH_2$—OH | hydrochloride: 139–141 (decomp.) | ethanol/ether |
| 32 | " | " | $CH_2CH_2$—$OCH_3$ | hydrochloride: 121.5–123 (decomp.) | " |
| 33 | " | " | $CH_2CH_2$—Cl | hydrochloride: 147–150 (decomp.) | " |
| 34 | " | " | $CH_2CH_2$—$SC_2H_5$ | hydrochloride: 114–116 (decomp.) | " |
| 35 | " | " | 2-chlorobenzyl (Cl on phenyl ring) | hydrochloride: 147.5–150 (decomp.) | " |
| 36 | " | " | $CH_2C_6H_5$ | hydrochloride: 130–132 (decomp.) | " |

TABLE I-continued

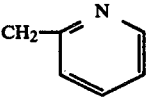

(Ia)

| No. | R | R₄ | R₅ | Melting point (°C.) | Recryst. Solvent |
|---|---|---|---|---|---|
| 37 | " | " | 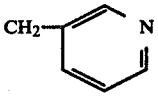 | dihydrochloride: 164–167 (decomp.) | ethanol |
| 38 | " | " | (pyridyl-CH₂-) | dihydrochloride: 141–143 (decomp.) | ethanol/ether |
| 39 | " | " | 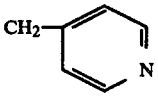 | dihydrochloride: 160–161.5 (decomp.) | " |
| 40 | " | CH₃ | " | 161–162 | ether |
| 41 | " | H | cyclohexyl | hydrochloride: 142–144 144 (decomp.) | ethanol/ether |
| 42 | 2-Cl | " | CH₂CH₂—SO₂C₂H₅ | hydrochloride: 135–137 (decomp.) | ethanol/ether |
| 43 | 2-Cl—5-CH₃O | " | i-C₃H₇ | hydrochloride: 131–133 (decomp.) | " |
| 44 | 2-CH₃—4-OH | " | " | hydrochloride: 142–144 (decomp.) | " |
| 45 | 2-CH₃—4-CH₃O | " | " | hydrochloride: 159–161 (decomp.) | " |

EXAMPLE 46

Sodium thioacetate (235 mg) was added to an ice-cooled, stirred solution of 1 g of 2-bromomethyl-3-(2-chlorophenyl)-6-ethoxycarbonyl-5,7-dimethyl-4(3H)-quinazolinone in 4 ml of dimethylformamide. After stirring for an additional 30 minutes, the mixture was poured into ice-water. The resulting precipitate was filtered off, washed with water, and dried in vacuo. The crude product was chromatographed on a column of silica gel using 5% ethyl acetate in benzene as an eluent to give 619 mg (yield, 62.5%) of 2-(acetylmercaptomethyl)-3-(2-chlorophenyl)-6-ethoxycarbonyl-5,7-dimethyl-4(3H)-quinazolinone melting at 103°–105° C. (recrystallized from methanol).

A portion (222 mg) of the above product was dissolved in 2 ml of methanol saturated with ammonia with ice-cooling under a nitrogen atmosphere. After stirring for 15 minutes, the solvent was then evaporated off. The residue was dried in vacuo and taken up with 10 ml of benzene. To this solution, 0.5 ml of methyl isocyanate was added, and the reaction mixture was then stirred at room temperature for 30 minutes under a nitrogen atmosphere and concentrated. The residue was chromatographed on silica gel to give 176 mg of an oily product. The oil was dissolved in absolute ether, and dry hydrogen chloride was introduced into the ethereal solution with ice cooling. The resulting precipitate was filtered off and dried to give 175 mg (yield, 70.7%) of 3-(2-chlorophenyl)-6-ethoxycarbonyl-5,7-dimethyl-2-(N-methylcarbamoylmercaptomethyl)-4(3H)-quinazolinone hydrochloride melting at 113°–120° C. MS m/e, 459, 424, 414, 367, 335 (base ion peak). NMR (ppm, in CDCl₃), 1.41 (3H, t), 2.42 (3H, s), 2.77 (3H, s), 2.86 (3H, s), 3.88 (2H, d), 4.41 (2H, q), 6.00 (1H, b), 7.3–7.7 (5H, m).

TESTS FOR BIOLOGICAL EFFECT (a) Hypotensive effect on anesthetized dogs

Groups of three to four normotensive dogs anesthetized with pentobarbital sodium were used in the experiments. The test compounds were dissolved in a minimum amount of ethanol, and the solutions were administered intravenously in the vein cannulated with a polyethylene tube. The mean blood pressures in the carotid artery were recorded using a pressure transducer and a recorder. The dose and reduction of blood pressure are tabulated in Table II. The hypotensive effect in Table II are a mean value obtained from at least three to four experiments.

TABLE II

| Test compound | Hypotensive Effect Δ(mmHg) dose (μg/kg) | | | | |
|---|---|---|---|---|---|
| No. | 1.0 | 3.0 | 10 | 30 | 100 |
| 1 | 3 | 6 | 22 | 43 | 51 |
| 2 | 24 | 48 | NT | NT | NT |
| 3 | 0 | 0 | 1 | 6 | 20 |
| 9 | 22 | 42 | NT | NT | NT |
| 10 | 10 | 25 | NT | NT | NT |
| 12 | 10 | 25 | NT | NT | NT |
| 14 | 8 | 10 | 25 | NT | NT |
| 18 | 5 | 10 | 28 | NT | NT |
| 19 | 20 | 35 | NT | NT | NT |
| 23 | 8 | 25 | NT | NT | NT |
| 27 | 0 | 0 | 8 | 18 | 25 |

TABLE II-continued

| Test compound No. | Hypotensive Effect Δ(mmHg) dose (μg/kg) | | | | |
|---|---|---|---|---|---|
| | 1.0 | 3.0 | 10 | 30 | 100 |
| 28 | 0 | 6 | 9 | 25 | NT |

NT = not tested

As shown in the Table II, the compound of the present invention exhibited a highly potent and dose-dependent hypotensive effect in anesthetized dogs.

Under the same conditions described above, papaverine, the compound described in U.S. Pat. No. 4,276,295 [e.g., 3-(2-chlorophenyl)-6-ethoxycarbonyl-2,5,7-trimethyl-4(3H)-quinazolinone and]6-ethoxycarbonyl-3-[2-(trifluoromethyl)phenyl]-2,5,7-trimethyl-4(3H)-quinazoline], and the compound described in U.S. patent application Ser. No. 263,898 [e.g., 3-(2-chlorophenyl)-6-ethoxycarbonyl-5,7-dimethyl-1-(2-(N,N-diethylamino)ethyl]-2,4(1H,3H)-quinazolinedione and 6-ethoxycarbonyl-3-[2-(trifluoromethyl)phenyl]-5,7-dimethyl-1-[2-(N,N-diethylamino)ethyl]-2,4(1H,3H)-quinazolinedione] did not exhibit a hypotensive effect in a dose under 100 μg/kg.

(b) Hypotensive effect on conscious spontaneously hypertensive rate

The test compounds were orally administered to groups of four to five of male spontaneously hypertensive rats (Wister Kyoto origin) weighing about 300 g and aged 15 to 20 weeks. The systolic blood pressure was measured by the tail-cuff method using a plethysmograph.

The compound of the invention produced a dose-dependent and long lasting hypotensive effect. The most pronounced effect was observed 4 to 6 hours after drug administration. The pD$_{30}$ (dose which decreases systolic blood pressure by 30 mmHg) was calculated as 2.8, 0.35, and 0.42 mg/kg for the compound No. 1, the compound No. 9, and the compound No. 2, respectively.

TEST FOR ACUTE TOXICITY

A suspension of a test compound in 0.5% CMC aqueous solution containing Tween 80 was orally administered to rats, and during 8 days the number of dead rats was counted. The results are shown below.

| Test compound No. | Dose (mg/Kg) | number of dead rats / number of test rats |
|---|---|---|
| 1 | 1200 | 2/6 |
| 1 | 1715 | 3/6 |
| 1 | 2450 | 3/6 |
| 1 | 3500 | 3/6 |
| 1 | 5000 | 5/6 |

The LD$_{50}$ of the compound No. 1 of the present invention was calculated as 2500 mg/kg. Thus, the toxicity of the compound of No. 1 and others of the present invention is very low.

What is claimed is:

1. A 4(3H)-quinazolinone compound of the formula (I)

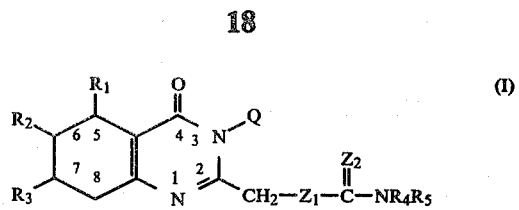

wherein
R$_1$ and R$_3$, independently from each other, represent lower alkyl;
R$_2$ represents lower alkoxycarbonyl;
Q represents phenyl or phenyl substituted by one, two or three members selected from the group consisting of halogen atoms, lower alkyl, lower alkoxy, di(lower)alkylamino, methylenedioxy, trifluoromethyl, hydroxyl, and nitro;
R$_4$ represents a hydrogen atom or lower alkyl;
R$_5$ represents a member selected from the group consisting of a hydrogen atom, cyclohexyl cyclohexymethyl alkyl, lower, lower halogenoalkyl, lower alkenyl, cyclohexenyl, (lower)alkoxy(lower)alkyl, hydroxy(lower)alkyl, (lower)alkylthio(lower)alkyl, (lower)alkylsulfinyl(lower)alkyl, (lower)alkylsulfonyl(lower)alkyl, di(lower)alkylamino(lower)alkyl, benzyl, phenethyl, pyridyl(lower)alkyl, furfuryl, phenyl, and phenyl substituted by a member selected from the group consisting of halogen atoms, lower alkyl, and lower alkoxy; and
Z$_1$ and Z$_2$, independently from each other, represent an oxygen or sulfur atom; and the pharmaceutically acceptable acid addition salts thereof.

2. A compound of claim 1, which is 3-(2-chlorophenyl)-6-ethoxycarbonyl-5,7-dimethyl-2-(N-methylcarbamoyloxymethyl)-4(3H)-quinazolinone.

3. A compound according to claim 1, which is 3-(2-chlorophenyl)-2-(N-ethylcarbamoyloxymethyl)-6-ethoxycarbonyl-5,7-dimethyl-4(3H)-quinazolinone.

4. A compound according to claim 1, which is 3-(2-chlorophenyl)-6-ethoxycarbonyl-5,7-dimethyl-2-(N-propylcarbamoyloxymethyl)-4(3H)-quinazolinone.

5. A compound according to claim 1, which is 3-(2-chlorophenyl)-6-ethoxycarbonyl-5,7-dimethyl-2-(N-isopropylcarbamoyloxymethyl)-4(3H)-quinazolinone.

6. A compound according to claim 1, which is 6-ethoxycarbonyl-3-(2-fluorophenyl)-5,7-dimethyl-2-(N-methylcarbamoyloxymethyl)-4(3H)-quinazolinone.

7. A compound according to claim 1, which is 6-ethoxycarbonyl-3-(2-fluorophenyl)-5,7-dimethyl-2-(N-ethylcarbamoyloxymethyl)-4(3H)-quinazolinone.

8. A compound according to claim 1, which is 6-ethoxycarbonyl-5,7-dimethyl-3-(2-methylphenyl)-2-(N-methylcarbamoyloxymethyl)-4(3H)-quinazolinone.

9. A compound according to claim 1, which is 6-ethoxycarbonyl-2-(N-ethylcarbamoyloxymethyl)-5,7-dimethyl-3-(2-methylphenyl)-4(3H)-quinazolinone.

10. A compound according to claim 1, which is 3-(2-chlorophenyl)-6-ethoxycarbonyl-2-[N-(2-hydroxy)ethylcarbamoyloxymethyl]-5,7-dimethyl-4(3H)-quinazolinone.

11. A compound according to claim 1, which is 3-(2-chlorophenyl)-6-ethoxycarbonyl-2-[N-(2-methoxy)-ethylcarbamoyloxymethyl]-5,7-dimethyl-4(3H)-quinazolinone.

12. A compound according to claim 1, which is 6-ethoxycarbonyl-2-(N-isopropylcarbamoyloxymethyl)-3-(2-methoxyphenyl)-5,7-dimethyl-4(3H)-quinazolinone.

13. A 4(3H)-quinazolinone compound according to claim 1 wherein
- $R_1$ and $R_3$, independently from each other, represent methyl, ethyl or propyl;
- $R_2$ represents methoxycarbonyl, ethoxycarbonyl, propoxycarbonyl, isopropoxycarbonyl, n-butoxycarbonyl or isobutoxycarbonyl;
- Q represents phenyl or phenyl substituted by up to three substituents selected from the group consisting of halogen, methyl, ethyl, propyl, methoxy, ethoxy, propoxy, n-butoxy, isobutoxy, dimethylamino, diethylamino, dipropylamino, methylenedioxy, trifluoromethyl, hydroxy and nitro;
- $R_4$ represents hydrogen, methyl, ethyl or propyl; and,
- $R_5$ represents hydrogen, methyl, ethyl, propyl, isopropyl, butyl, isobutyl, tert-butyl, amyl, isoamyl, hexyl, cyclohexyl, cyclohexylmethyl, fluoromethyl, 2-fluoroethyl, 3-fluoropropyl, 2-chloroethyl, 3-chloropropyl, 3-bromoethyl, allyl, 2-butenyl, 3-hexenyl, cyclohexenyl, $(C_1-C_3)$alkoxy$(C_1-C_4)$alkyl, hydroxy$(C_1-C_4)$alkyl, $(C_1-C_3)$alkylthio$(C_1-C_4)$alkyl, $(C_1-C_3)$alkylsulfinyl$(C_1-C_4)$alkyl, $(C_1-C_3)$alkylsulfonyl$(C_1-C_4)$alkyl, di-$(C_1-C_3)$alkylamino$(C_1-C_4)$alkyl, benzyl, phenethyl, 2-pyridylmethyl, 3-pyridylmethyl, 4-pyridylmethyl, 2-furfuryl, 3-furfuryl, 4-furfuryl, phenyl, halophenyl, methylphenyl, ethylphenyl, methoxyphenyl, ethoxyphenyl or propoxyphenol.

14. A compound according to claim 13 wherein $R_1$ and $R_3$ are each methyl and $R_2$ is ethoxycarbonyl.

15. A compound according to claim 14 wherein $Z_1$ and $Z_2$ are each oxygen.

16. A compound according to claim 14 wherein $Z_1$ and $Z_2$ are each sulfur.

17. A compound according to claim 13 wherein $Z_1$ and $Z_2$ are each oxygen.

18. A compound according to claim 13 wherein $Z_1$ and $Z_2$ are each sulfur.

19. A pharmaceutical composition suitable for the treatment of hypotension composed of an effective amount of a 4(3H)-quinazolinone compound and a pharmaceutically acceptable diluent or carrier, said 4(3H)-quinazolinone compound being selected from the group consisting of the compounds of the following formula

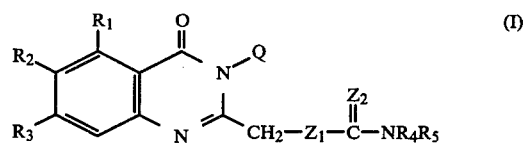

wherein
- $R_1$ and $R_3$, independently from each other, represent lower alkyl;
- $R_2$ represents lower alkoxycarbonyl;
- Q represents phenyl or phenyl substituted by one, two or three members selected from the group consisting of halogen atoms, lower alkyl, lower alkoxy, di(lower)alkylamino, methylenedioxy, trifluoromethyl, hydroxyl, and nitro;
- $R_4$ represents a hydrogen atom or lower alkyl;
- $R_5$ represents a member selected from the group consisting of a hydrogen atom, lower alkyl, cyclohexyl, cyclohexymethyl, halogenoalkyl, lower alkenyl, lower cyclohexenyl (lower)alkoxy(lower)alkyl, hydroxyl(lower)alkyl, (lower)alkylthio(lower)alkyl, (lower)alkylsulfinyl(lower)alkyl, (lower)alkylsulfonyl(lower)alkyl, di(lower)alkylamino(lower)alkyl, benzyl, phenetyl, pyridyl(lower)alkyl, furfuryl, phenyl, and phenyl substituted by a member selected from the group consisting of halogen atom, lower alkyl, and lower alkoxy; and
- $Z_1$ and $Z_2$, independently from each other, represent an oxygen or sulfur atom and the pharmaceutically acceptable acid addition salts thereof.

* * * * *

UNITED STATES PATENT AND TRADEMARK OFFICE
CERTIFICATE OF CORRECTION

PATENT NO. : 4,451,467
DATED : May 29, 1984
INVENTOR(S) : ISHIKAWA, ET AL.

It is certified that error appears in the above—identified patent and that said Letters Patent is hereby corrected as shown below:

Claim 1, column 18, line 20, after "hydrogen atom," insert --lower alkyl,--; after "cyclohexyl", insert --,--;

lines 20 and 21, after "cyclohexylmethyl", delete "alkyl, lower".

Claim 19, column 20, line 27, before "halogenoalkyl", insert --lower--.

Claim 13, column 19, line 29 (last line in claim), delete "propoxyphenol", insert --propoxyphenyl--.

Signed and Sealed this
Twenty-third Day of December, 1986

*Attest:*

DONALD J. QUIGG

*Attesting Officer*  *Commissioner of Patents and Trademarks*